US008444936B2

(12) United States Patent
Taniguchi et al.

(10) Patent No.: US 8,444,936 B2
(45) Date of Patent: May 21, 2013

(54) AUTOANALYZER AND PIPETTING NOZZLE FOR AUTOANALYZER (75) Inventors: Shinichi Taniguchi, Tokyo (JP); Akihiro Nojima, Yokohama (JP); Takashi Inoue, Yokohama (JP); Hiroaki Ishizawa, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/147,152

(22) PCT Filed: Jan. 5, 2010

(86) PCT No.: PCT/JP2010/050017
§ 371 (c)(1),
(2), (4) Date: Jul. 29, 2011

(87) PCT Pub. No.: WO2010/109927
PCT Pub. Date: Sep. 30, 2010

(65) Prior Publication Data
US 2011/0300035 A1 Dec. 8, 2011

(30) Foreign Application Priority Data
Mar. 27, 2009 (JP) .................. 2009-079897

(51) Int. Cl.
*B01L 3/02* (2006.01)
(52) U.S. Cl.
USPC .............. 422/519; 422/63; 422/64; 422/65; 422/66; 422/67; 422/501; 422/524

(58) Field of Classification Search
USPC .............. 422/501, 63–67, 519, 524; 436/180
See application file for complete search history.

(56) References Cited

U.S. PATENT DOCUMENTS

| 4,357,301 | A | 11/1982 | Cassaday et al. | |
|---|---|---|---|---|
| 6,069,027 | A * | 5/2000 | Mertol et al. | 438/118 |
| 6,613,131 | B2 * | 9/2003 | Ujita et al. | 96/6 |
| 6,685,301 | B2 * | 2/2004 | Eida et al. | 347/45 |
| 7,074,314 | B2 * | 7/2006 | Eida et al. | 205/206 |
| 7,194,015 | B2 * | 3/2007 | Hayashikawa et al. | 372/55 |
| 7,264,346 | B2 * | 9/2007 | Nishino et al. | 347/102 |
| 2001/0007171 | A1 * | 7/2001 | Kinoshita | 29/729 |
| 2002/0122096 | A1 * | 9/2002 | Eida et al. | 347/45 |
| 2003/0066426 | A1 * | 4/2003 | Ujita et al. | 96/6 |
| 2004/0041883 | A1 * | 3/2004 | Eida et al. | 347/45 |
| 2005/0012778 | A1 * | 1/2005 | Nishino et al. | 347/29 |
| 2006/0049147 | A1 * | 3/2006 | Hayashikawa et al. | 219/121.6 |
| 2006/0183244 | A1 | 8/2006 | Matsubara et al. | |
| 2010/0150782 | A1 | 6/2010 | Fukushima et al. | |

FOREIGN PATENT DOCUMENTS

| DE | 68920067 T2 | 5/1995 |
|---|---|---|
| EP | 0707623 A1 | 4/1996 |
| JP | 58-44349 | 3/1983 |
| JP | 01-274866 | 11/1989 |

(Continued)

*Primary Examiner* — Brian R Gordon
*Assistant Examiner* — Shogo Sasaki
(74) *Attorney, Agent, or Firm* — McDermott Will & Emery LLP (57) ABSTRACT

There is provided a highly reliable autoanalyzer less liable to sample and reagent carry-over and capable of preventing contamination and precisely pipetting samples and reagents. Using a sample pipetting nozzle 27 having water-repellent surfaces, a sample is pipetted from a sample cell 25 to a reaction cell 4 having a hydrophilic bottom face.

4 Claims, 8 Drawing Sheets

FOREIGN PATENT DOCUMENTS

| | | |
|---|---|---|
| JP | 3-75827 | 12/1991 |
| JP | 1706358 | 10/1992 |
| JP | 2000-329771 | 11/2000 |
| JP | 2001-208762 | 8/2001 |
| JP | 2004-136236 | 5/2004 |
| JP | 2007-183240 | 7/2007 |
| JP | 2008-256525 | 10/2008 |
| JP | 2009-058437 | 3/2009 |
| WO | WO2009028469 | * 3/2009 |

* cited by examiner

AUTOANALYZER AND PIPETTING NOZZLE FOR AUTOANALYZER

RELATED APPLICATIONS

This application is the U.S. National Phase under 35 U.S.C. §371 of International Application No. PCT/JP2010/050017, filed on Jan. 5, 2010, which in turn claims the benefit of Japanese Application No. 2009-079897, filed on Mar. 27, 2009, the disclosures of which Applications are incorporated by reference herein.

TECHNICAL FIELD

The present invention relates to an autoanalyzer for medical diagnosis used to perform biochemical analysis, immune assay, and the like, and to a pipetting nozzle used for the auto analyzer.

BACKGROUND ART

In a clinical examination for medical diagnosis, biochemical analysis and immunological analysis are performed on protein, sugar, lipid, enzyme, hormone, inorganic ions, disease markers, and the like in a biological sample, such as blood and urine. In addition, a wide variety of analysis methods is used, including a method using DNA probes and a method of measuring DNA and the like by means of electrophoresis. Since a plurality of inspection items needs to be processed with high reliability and at high speed in a clinical examination, most of the items are processed using an autoanalyzer. As the autoanalyzer, there has been conventionally known, for example, a biochemical autoanalyzer in which a reaction liquid prepared by mixing a desired reagent into a sample, such as blood serum, and reacting the reagent with the sample is used as an object of analysis to conduct biochemical analysis by measuring the absorbance of the reaction liquid. This type of biochemical autoanalyzer is provided with a container for housing samples and reagents, a reaction cell into which a sample and a reagent are injected, a pipetting mechanism for automatically injecting a sample and a reagent into the reaction cell, an automatic agitating mechanism for mixing the sample and the reagent within the reaction cell, a mechanism for measuring the spectrum of a sample the reaction of which is in progress or completed, an automatic cleaning mechanism for suctioning and discharging a reaction liquid after the completion of spectrum measurement to clean the reaction cell, and the like (see, for example, Patent Literature 1).

In the field of autoanalyzers, reducing the amount of sample and reagent has become a technical issue. That is, an amount of sample that can be allocated to a single item has been reduced as the number of analysis items increases. In some cases, the sample itself is valuable, and therefore, cannot be prepared in large amounts. Accordingly, an analysis of microscale samples which has heretofore been considered a high-level analysis has become a routine practice. In addition, reagents generally tend to be costly as the details of analysis become increasingly sophisticated. Thus, there is a demand for a reduction in the amounts of reagents also from the viewpoint of costs. Such reductions in the amounts of samples and reagents also serve as a strong incentive to promote the miniaturization of reaction cells. In addition, the miniaturization of reaction cells and reductions in the amounts of required samples and reagents, offer the advantages of leading to an improvement in analysis throughputs and a reduction in the amount of waste liquid. In that case, there is the need to precisely pipette microscale samples and reagents.

Here, a mechanism for automatically injecting samples and reagents in a commonly used autoanalyzer is referred to as a pipetting nozzle or a pipetting probe, and is generally made of metal, glass or resin. In addition, a reaction cell (also referred to as a cell, a reaction container or a well) used in the commonly used autoanalyzer is generally formed of glass, synthetic resin (plastic), or the like. According to Patent Literature 2, a suction/discharge method is available as one example of pipetting methods. By suctioning and discharging a sample by using a sample pipetting nozzle, the sample can be transferred, for example, from a container, such as a blood sampling tube, in which the sample is stored, to a reaction cell for reacting the sample with a reagent.

Examples of the sample pipetting nozzle include a reusable metal pipetting nozzle and a disposable plastic pipetting nozzle. The disposable nozzle is convenient in that the nozzle need not be cleaned at each time of use, but is not economical. The reusable nozzle is economical but needs to be cleaned at each time of reuse. Hence, insufficient cleaning results in that a nozzle to which residues of the sample are attached is used the next time. In this case, there arises the problem of so-called carry-over in which residues of the sample get mixed in with a newly collected sample.

As another example of pipetting methods, an ink-jet method shown in Patent Literature 3 is available. A trend in the field of autoanalyzers is toward further reductions in the amounts of samples and reagents. In addition, a demand for the miniaturization of apparatus continues to grow further. Samples are blood serum and urine and the minimum pipetted amount of each of these liquid samples has fallen below 2 µL in recent years. In addition, the diameter of nozzles has been reduced to approximately 0.5 mm. As the diameter is reduced in this way, a ratio of the contact area to the volume of a nozzle increases. Thus, there is the need to control substances adsorbed onto the surfaces of the nozzle. In this case, the nozzle is used after cleaning off substances adsorbed onto the inner and outer surfaces of the nozzle with a cleaning liquid using water or surfactant, when a plurality of samples is successively measured. This cleaning may be carried out at each time of pipetting or at least at the time of transfer from one sample to another. As cleaning methods, water or a cleaning liquid is soused for the outer surfaces of the nozzle or water is pushed out from the back end of a flow path within the nozzle for the inner surfaces thereof. As another cleaning method, the nozzle is cleaned by performing suction and discharge by using a cleaning liquid containing a surfactant at the end of a certain period of time, for example, at the end of a day's work.

CITATION LIST

Patent Literature

Patent Literature 1: JP Patent No. 1706358
Patent Literature 2: JP Patent Publication (Kokai) No. 2001-208762
Patent Literature 3: JP Patent Publication (Kokai) No. 2000-329771

SUMMARY OF INVENTION

Technical Problem

Along with a reduction in the amount of sample to be analyzed, there have emerged new issues which did not matter before. These issues are accuracy and repeatability when microscale samples are pipetted. Accordingly, if a sample pipetting nozzle made of metal, such as stainless steel (for example, SUS 304) is directly used, accuracy and repeatability are degraded when a microscale sample is pipetted. In the case of microscale samples 0.5 µL or less in volume, pipetting can be said to be "transfer" of the samples from a nozzle to a destination of pipetting. That is, pipetting refers to transferring a droplet of a sample formed at a tip of a sample pipetting nozzle to a destination of pipetting, for example, a cell bottom. As described above, weighing accuracy needs to be maintained even when a microscale sample is pipetted. However, the inventors have found, as a new problem, that a variation occurs in the amount of pipetting when a sample 0.5 µL or less in volume is pipetted.

Figure 1:
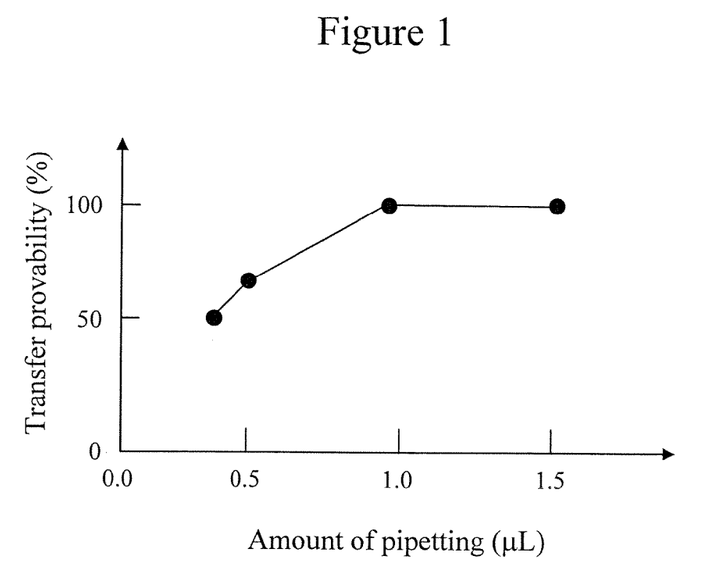
FIG. 1 is a drawing showing a relationship between the amount of pipetting and pipetting accuracy.

The following are experimental results studied in advance. A predetermined amount of water was ejected from an SUS syringe needle and transferred onto a surface of cycloolefin polymer. The amount of water transferred onto the surface of cycloolefin polymer was read from an image of a contact angle meter. For the contact angle meter, Drop Master 500 made by Kyowa Interface Science was used. A droplet of a predetermined amount of pure water was formed at a syringe tip to transfer the pure water to a surface of cycloolefin polymer. FIG. 1 shows the amount of pipetting and transfer (pipetting) probability. Transfer probability here refers to the probability of a droplet of a predetermined pipetted amount of water formed at a tip of the syringe needle being transferred onto a surface of the cycloolefin polymer when this water is placed in contact with the surface. The number of experiments is 10. The axis of abscissas in FIG. 1 represents the amount of pipetting and the axis of ordinates represents transfer probability (%). The results of the experiments showed that the transfer probability was 100% when the pipetted amount was 1.5 µL and 1.0 µL. However, the transfer probability was 60% when the pipetted amount was 0.5 µL, and decreased to 50% when the pipetted amount was reduced to 0.4 µL. That is, it has proved that if the pipetted amount falls below 0.5 µL, the transfer probability decreases.

In addition, there is concern, in association with the improvement of analysis methods, that a substance adsorbed onto a sample pipetting nozzle may break loose at the time of pipetting the next sample to be measured and get mixed in with the sample if the nozzle is insufficiently cleaned in cases where a lower-concentration substance contained in the sample is measured. This is generally referred to as carry-over. For carry-over, an allowable range is determined according to a system's range of detection. That is, assume that the substance to be measured is lower in concentration than detection sensitivity in the next sample. If the residue a of a previous sample having broken loose has a concentration of $a/V$ with respect to the volume V of the next sample and this concentration is greater than the detection sensitivity, then this situation is recognized as carry-over.

However, the amount of substance to be carried over is determined by a relationship between the amount of substance adsorbed onto surfaces of the pipetting nozzle and the amount of adsorbed substance that elutes into the next sample. In addition, this relationship does not hold true if a surface condition of the pipetting nozzle differs. Hence, an autoanalyzer is equipped with a mechanism for cleaning a pipetting nozzle to clean outer walls of the pipetting nozzle, in order to clean off the attached sample.

Figure 2:
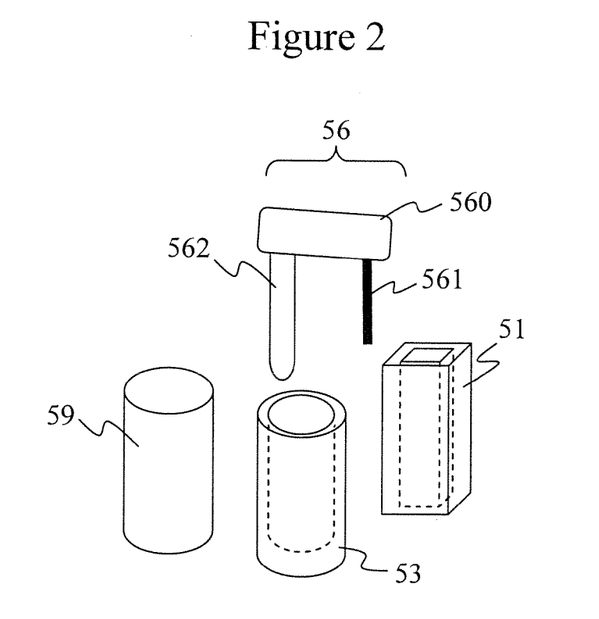
FIG. 2 is a schematic view of a sample pipetting mechanism of an autoanalyzer.

FIG. 2 is a schematic view of a sample pipetting mechanism of an autoanalyzer. A sample pipetting mechanism 56 includes an arm 560, a pillar 562 and a sample pipetting nozzle 561. The pipetting nozzle suctions a sample, such as blood serum or urine, from a sample cell 53 and discharges the sample into a reaction cell 51, thus completing pipetting. Thereafter, the sample pipetting nozzle 561 is cleaned, as necessary, by a cleaning mechanism 59.

Figure 3:
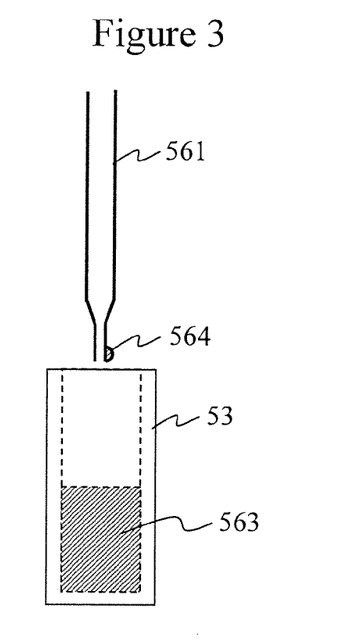
FIG. 3 is a drawing illustrating the way pipetting is performed in automatic analysis.
Figure 4:
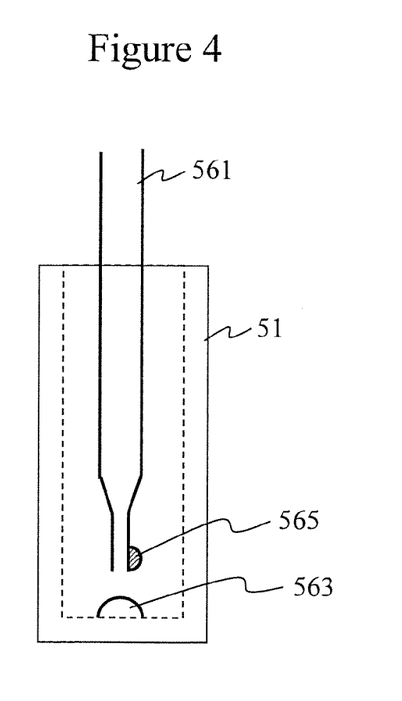
FIG. 4 is a drawing illustrating the way pipetting is performed in automatic analysis.
Figure 5:
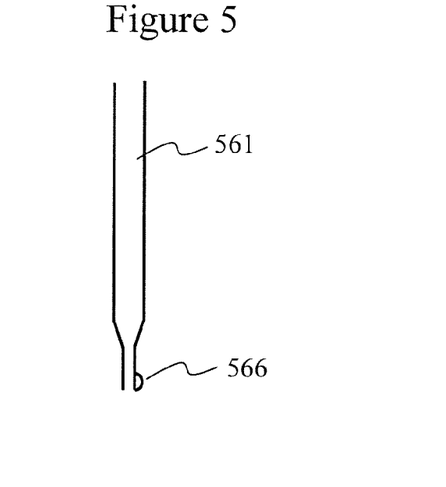
FIG. 5 is a drawing illustrating the way pipetting is performed in automatic analysis.

As the result of visually inspecting the pipetting mechanism operated in this way and quantifying a variation in pipetted amounts, causes for degradation in the accuracy and repeatability of sample pipetting have been found to be as follows: The causes will be described using FIGS. 3 to 5. FIG. 3 is a drawing schematically illustrating the way a sample is suctioned from a sample tube, FIG. 4 is a drawing schematically illustrating the way the sample is discharged into a cell, and FIG. 5 is a drawing schematically illustrating a post-cleaning condition of the sample pipetting nozzle. FIGS. 3, 4 and 5 are schematic drawings respectively corresponding to Causes (1), (2) and (3).

Cause (1): As illustrated in FIG. 3, an adhering sample 564 attaches to an outer wall surface of the sample pipetting nozzle 561 when a sample 563 is suctioned and taken up from the sample cell 53.

Cause (2): As illustrated in FIG. 4, the sample is not entirely discharged but an adhering sample 565 is present on an outer wall of the sample pipetting nozzle 561 when the suctioned sample 563 is discharged into the cell 51.

Cause (3): As illustrated in FIG. 5, rinse water 566 attaches to an outer wall of the sample pipetting nozzle 561.

The inventors have also found that the hydrophilicity of outer walls of the sample pipetting nozzle increases due to one or more than one of Causes (1) to (3), the sample attaches to an outer wall of the nozzle when transferred to the cell, and the nozzle carries over the sample, thus causing degradation in pipetting accuracy thereafter.

If a reduction in the pipetted amount of sample progresses further in the future, these causes are predicted to become major issues. In order to cope with the trend of miniaturization in autoanalyzers and reductions in the amounts of samples and reagents, problems due to Causes (1) to (3) described above need to be solved. The present invention has been accomplished to meet this requirement.

Solution to Problem

The inventors of the present invention water-repellency treated outer wall surfaces of a sample pipetting nozzle and hydrophilized an area of a cell where a sample was pipetted. Consequently, the inventors have found that these treatments improve the accuracy and repeatability of pipetting. By water-repellency treating the outer wall surfaces of the sample pipetting nozzle and hydrophilizing the pipetting area of the cell, the sample is reliably transferred to the cell and pipetting accuracy is not degraded. In addition, rinse water doses not attach to the nozzle since the nozzle is water-repellent. Inner wall surfaces of the nozzle may be water-repellency treated along with the outer wall surfaces. Concurrent use of the water-repellency treated nozzle and a reaction cell with a hydrophilization-treated pipetting area improves pipetting accuracy when a microscale sample is pipetted in an autoanalyzer.

Note that an ink-jet method is available as another example of pipetting methods. This method is not suitable for pipetting microscale samples, however, since an amount of sample larger than the amount desired to be discharged needs to be temporarily stored in a sample reservoir. In addition, the autoanalyzer generally analyzes a variety of samples in steps of small volumes. Consequently, in the ink-jet method in which the sample is temporarily stored in the sample reservoir and then discharged, contamination of other samples is not ignorable if a certain sample attaches to the sample reservoir. In addition, cleaning the sample reservoir to which such a contaminant has attached leads to a cost increase. Accordingly, the present invention will be described with a focus on a pipetting mechanism using a suction/discharge method. It should be noted however that the inventors do not intend to preclude application of the present invention to other pipetting methods, including the ink-jet method.

Advantageous Effects of Invention

According to the present invention, it is possible to perform uniform water-repellent plating treatment on outer wall surfaces of a sample pipetting nozzle. Thus, the nozzle's outer wall surfaces exhibit uniform water repellency. Since the outer wall surfaces exhibit high water repellency, the nozzle is superior in cutting off sample drippings at the time of pipetting and less liable to sample carry-over.

By concurrently using the nozzle with water-repellency treated surfaces and a cell with a hydrophilization-treated pipetting area, it is possible to upgrade the accuracy and repeatability of sample pipetting at the time of performing automatic analysis. Since contamination of the outer wall surfaces of the nozzle by a sample can be prevented, it is possible to prevent mutual contamination between analyses, thereby improving data reliability. These advantageous effects contribute to both reducing the amounts of samples and reagents used and reducing the running cost of an autoanalyzer.

DESCRIPTION OF EMBODIMENTS

A description will be given of the water-repellency treatment of surfaces of a pipetting nozzle and the hydrophilization treatment of a pipetting area of a reaction cell.

In some autoanalyzers, a tip of a pipetting nozzle needs to have electrical conductivity, in order to detect a fluid level and control the height of the nozzle. Accordingly, SUS 304, for example, needs to be selected as the material of the pipetting nozzle. In addition, in the case of an autoanalyzer requiring a fluid level detection function based on electrical conductivity, high water repellency needs to be imparted to surfaces of the nozzle, while still maintaining electrical conductivity. On the other hand, if water repellency improvements by commonly used chemical coating or chemical reaction are excessively made to inner wall surfaces or outer wall surfaces of the pipetting nozzle or to both thereof, surface electrical conductivity is lost due to the formation of insulating films. Consequently, it is no longer possible to detect a fluid level.

Hence, the inventors have conceived of applying nickel-fluorine resin eutectoid plating treatment to outer wall surfaces of the pipetting nozzle. In this method, nickel-teflon electroless plating is performed on surfaces of the pipetting nozzle. As the result of nickel being present in a surface plated layer, it is possible to achieve all objectives, i.e., high electrical conductivity, high water repellency based on fluorine resin, and strong junction to the surfaces. Objects on which surface treatment is performed can be inner wall surfaces and outer wall surfaces of the pipetting nozzle. From the results of exploratory experiments, however, it proved that excellent results of pipetting were obtained by applying uniform water-repellent plating treatment to the outer wall surfaces.

A plated layer of several micrometers in thickness can be formed by performing nickel-fluorine resin eutectoid plating treatment on a metal surface. Thus, it is possible to greatly improve water repellency. Actual electron microscope (SEM) observation of a cross-section surface layer of a pipetting nozzle on the surfaces of which nickel-fluorine resin eutectoid plating treatment has been performed showed that obviously, an approximately 5 micrometers-thick plated layer was formed. In addition, substantial improvement was confirmed in a contact angle with respect to water, and therefore, water repellency improved. Elemental analysis of the plated layer showed that there were detected constituents derived from plating, i.e., fluorine and phosphorous, which were inherently not existent in SUS surfaces. Note that the plating-treated pipetting nozzle is free from damage in appearance and poses no problems for automatic analysis.

As described above, according to the present invention, it is possible to water-repellency treat surfaces of a pipetting nozzle for an autoanalyzer. At the same time, the pipetting nozzle has electrical conductivity. In addition, use of the pipetting nozzle of the present invention provides high accuracy and repeatability in sample pipetting. In addition to a pipetting nozzle plated for electrical conductivity, it is also possible to use a nozzle coated with diamond-like carbon (DLC), a nozzle to which a silane coupling agent having a long-chain alkyl group is fixed to an appropriate thickness, and a nozzle on which water-repellent molecules are vapor-deposited. In these surface-modified nozzles, electrical conductivity can still be maintained by setting the film thickness of the nozzles to as thin as 100 nm or less.

The inventors have found that in a sample pipetting mechanism, it is effective in improving pipetting accuracy to preliminarily hydrophilize a surface of a cell where a sample is pipetted, in addition to the above-described water-repellency treatment of a nozzle. The reason for this is that even if a sample or rinse water attaches to outer walls of a nozzle and the hydrophilicity of the nozzle's outer walls increases through a plurality of times of use, a cell, which is a counterpart of sample transfer, allows the sample to be retained as long as the hydrophilicity of a pipetting area of the cell is high. Corona discharge was particularly effective as a method for hydrophilizing a plastic reaction cell. When approximately 0.2 µL of a microscale sample is pipetted, the pipetting nozzle does not carry over the sample, if the area where the sample is pipetted is hydrophilic. In addition, pipetting accuracy is improved further by correctly setting an area to be hydrophilized.

Note that sample pipetting nozzles to be used in an autoanalyzer are generally mounted in large quantity on the autoanalyzer, in order to improve the number of analyses (throughputs) per unit time in automatic analysis. In addition, in order to improve the accuracy and repeatability of analysis, the water repellency of water-repellency treated surfaces of a nozzle is required to be uniform, and a nozzle-to-nozzle variation in water-repellency treatment is required to be suppressed. At the same time, the degree of hydrophilization of the hydrophilization-treated cell surface is required to be uniform, and a cell-to-cell variation in hydrophilization treatment is required to be suppressed. The above-described water-repellency treatment of a nozzle and the above-described hydrophilization treatment of a cell can also meet these requirements.

Next, the present invention will be described in more detail according to embodiments, but is not limited to the embodiments to be described hereinafter.

(1) Water-Repellency Treatment of Outer Wall Surfaces of Sample Pipetting Nozzle by Water-Repellent Plating Treatment A sample pipetting nozzle for an autoanalyzer (hereinafter referred to as the "nozzle") was fabricated using stainless steel (SUS 304) as the material thereof. The material of the nozzle may be one type of material selected from the group consisting of aluminum, SUS, other types of metal, glass, resin, and the like. In order to detect a fluid level, a tip of the nozzle needs to be electrically conductive. In addition, it is desirable to select SUS 304 from the viewpoint of processability, durability, and resistance to corrosion. Although an example of water-repellency treatment of the sample pipetting nozzle will be described here, the same surface treatment may be applied to a reagent pipetting nozzle.

Figure 6:
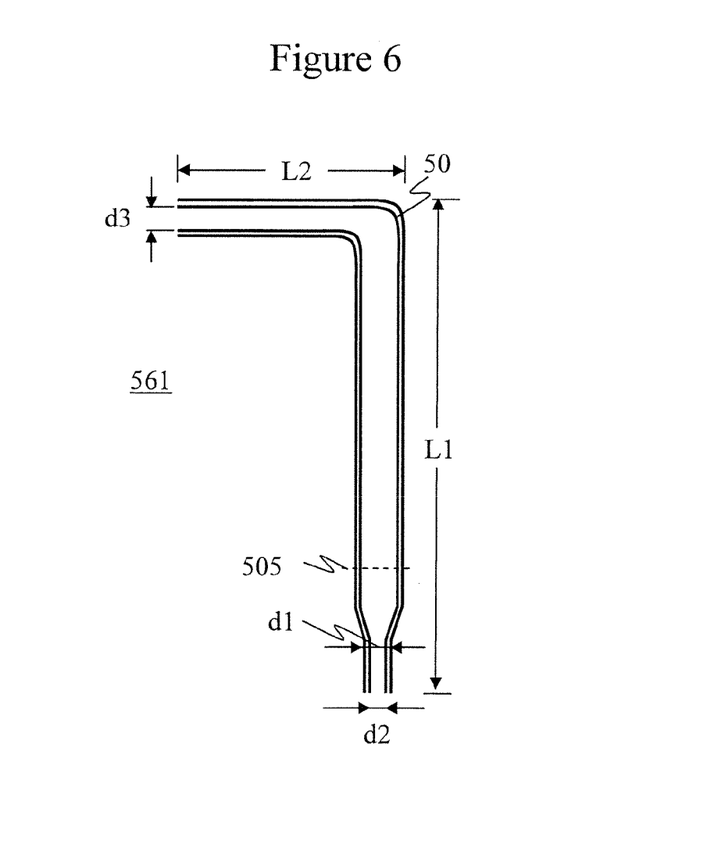
FIG. 6 is a schematic view of a sample pipetting nozzle.
Figure 7:
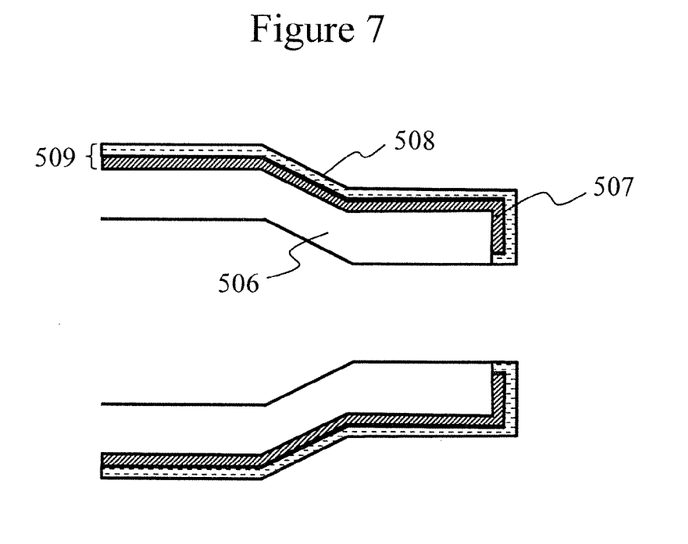
FIG. 7 is a cross-sectional view of a water-repellency plating treated nozzle tip.

In the present embodiment, a sample pipetting nozzle fabricated by using SUS 304 as the material thereof and by machining, bending and polishing the material was used. FIG. 6 illustrates a cross-sectional view of the sample pipetting nozzle. One type of pipetting nozzle 561 has an L-shaped structure. A length L1 of the longer portion of the L-shaped structure is 100 mm and a length L2 of the shorter portion thereof is 50 mm. A tip of the nozzle is taper-structured and has an outer diameter d1 of, for example, φ0.5 mm. The inner diameter d2 of the extra-fine tip is 0.3 mm. An inner diameter d3 of the opposite end of the pipetting nozzle is 0.5 mm. Although the tip of the nozzle is taper-structured in the present embodiment, the tip may have a straight-line structure. FIG. 7 is a cross-sectional view taken by cutting the nozzle's tip at a position denoted by a dashed line 505 after water-repellent plating treatment.

When a sample was pipetted using this SUS 304 sample pipetting nozzle, such phenomena as shown in FIGS. 3 to 5 occurred in some cases. The nozzle 561 fabricated by means of machining and polishing suctions a desired amount of sample from a sample tube, and discharges the sample into a reaction cell. After coming into contact with a bottom surface of the reaction cell, the nozzle retaining the desired amount of sample discharges the sample. Then, the nozzle is lifted. When a new sample pipetting nozzle was used, outer walls of the pipetting nozzle became hydrophilized, though not actualized, as the nozzle was kept in use. Accordingly, when the nozzle discharged the sample, the sample attached to an outer wall surface of the nozzle in whole or in part, thus forming sample attachments and/or rinse water attachments and carrying them over in some cases. Thus, there was a case that pipetting accuracy thereafter went out of order.

Hence, the inventors decided to perform water-repellent plating treatment on outer wall surfaces of the nozzle 561. From the viewpoint of durability and resistance to corrosion, it is understood that water-repellent plating treatment can retain water repellency stronger than that provided by water-repellent coating based on mere chemical immersion, coating or spraying. For the water-repellent plating treatment, a method called nickel-teflon eutectoid plating was adopted. Alternatively, nickel particle implantation referred to as nickel strike may be preliminarily performed on an SUS surface, and then nickel-teflon electroless plating may be carried out.

FIG. 7 illustrates a cross-sectional view of the tip of the nozzle after water-repellent plating treatment. As the result of water-repellent plating treatment, it is possible to provide a foundation layer 507, such as a nickel layer, on outer wall surface of an SUS 506, and provide a water-repellent layer 508 and a plated layer 509 on surfaces of the foundation layer. Even in such a multilayer structure as described above, the nozzle exhibits water repellency as long as the outermost surface of the structure is a water-repellent layer. On the other hand, it was possible to maintain the SUS surface without performing the above-described water-repellent plating treatment on inner wall surfaces of the nozzle. Mirror polishing may be performed on the SUS inner wall surfaces to improve the planarity thereof. As the result of this treatment, it is possible to make the outer wall surfaces of the nozzle uniformly water-repellent and the inner wall surfaces uniformly hydrophilic.

Note that the water-repellent plating treatment of the nozzle includes a step of immersing the nozzle in a plating solution. At this time, there is concern that the plating solution enters the nozzle, thus causing inner wall surfaces thereof to be plating-treated. Hence, the inventors have conceived of fabricating such a nozzle as illustrated in FIG. 8, performing water-repellent plating only on outer wall surfaces of the nozzle, and then machining the nozzle.

Figure 8:
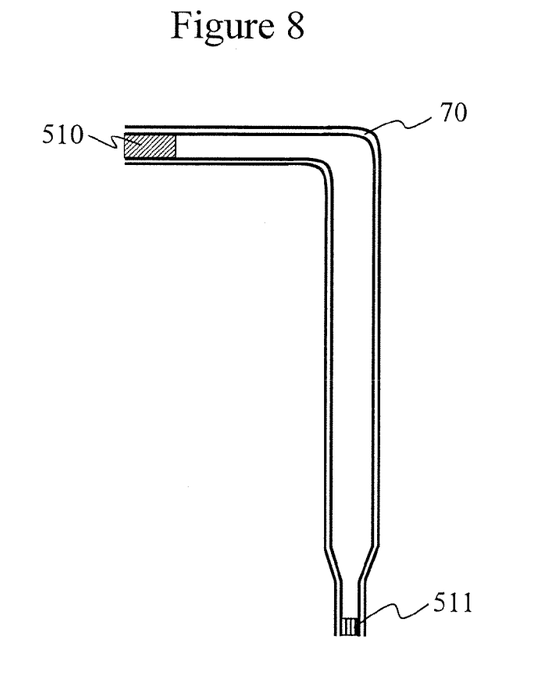
FIG. 8 is a schematic view of a nozzle.

A nozzle 70 illustrated in FIG. 8, unlike the above-described nozzle 561, has margins 510 and 511 respectively on one and the other ends thereof and openings of the nozzle are closed preliminarily. This is because an SUS nozzle before hole making may be used to allow the margins 510 and 511 to be formed of SUS. Alternatively, the openings may be closed by plugging both ends of the nozzle after hole making with rubber, resin or the like. Water-repellent plating treatment was performed on this nozzle 70 by using Processes 1 to 3 described below.

Process 1: Performing water-repellent plating treatment on the nozzle 70 the both ends of which are closed.

Process 2: Cutting both ends of the nozzle treated in Process 1, thereby fabricating a perforated nozzle having a desired overall length.

Process 3: Performing water-repellent plating treatment, as necessary, on cross sections of both openings.

Outer wall surfaces of the pipetting nozzle fabricated using the above-described processes are water-repellent. In addition, hydrophilicity which metal inherently has can be utilized for inner wall surfaces of the nozzle. If water-repellent plating treatment is performed on a nozzle whose openings at both ends are not closed, the plating solution may get inside the nozzle. Consequently, water-repellent plating treatment may be nonuniformly performed on inner wall surfaces of the nozzle, and therefore, the nozzle is not preferable. In this embodiment, a nozzle in which only the outer wall surfaces thereof were subjected to water-repellent plating treatment was fabricated.

Note however that the following cases may apply to even a pipetting nozzle with openings left not plugged. For example, (1) no problem is caused at the time of pipetting even if a plating substance somewhat attaches to the inner wall surfaces.

(2) A plating substance attached to the inner wall surfaces is removed by polishing.

(3) The inner wall surfaces are uniformly plated.

(4) Only the outer walls are plated by masking the openings at both ends.

In addition to these cases, it is possible to plate a nozzle material in a state of a perforated pipe before being shaped into a nozzle form, and then perform bending and drawing work on the pipe. In the present embodiment, a nozzle fabricated using Processes 1 to 3 discussed above will be described in detail.

For contact angle measurement, Drop Master 500 made by Kyowa Interface Science was used. 0.1 µL of pure water was dropped on an outer wall surface of the nozzle with a syringe, to measure static contact angles one second after droplet deposition by a three-point method. For the measurement, the surface was measured in steps of 1 mm to determine an average value of six sites. As a result, a contact angle of the water-repellent plating treated nozzle with respect to the water was 120 degrees. On the other hand, a contact angle of an SUS 304 sample pipetting nozzle before water-repellent plating treatment with respect to the water was 90 degrees. Consequently, water repellency was improved by water-repellent plating treatment.

TABLE 1

| Sample | Contact angle (degree) |
| --- | --- |
| After water-repellent plating treatment | 120 |
| Before water-repellent plating treatment | 90 |

Next, Table 2 shows results of electron microscope observation and elemental analysis conducted on a water-repellent plating treated nozzle by means of SEM-EDAX (electron microscope-based elemental analysis). For measurement, Model S2460 made by Hitachi, Ltd. was used. In order to measure a film thickness of plating, an SEM-EDAX observation was conducted after cutting the nozzle.

TABLE 2

| | Presence/absence of element | | | |
| --- | --- | --- | --- | --- |
| Site of nozzle | Nickel | Fluorine | Phosphorous | Thickness (µm) |
| Outermost layer | Present (abundant) | Present | Present | 2 |
| Foundation layer | Present (abundant) | Present | Present | 3 |
| SUS layer | Present (scarce) | Absent | Absent | 95 |

As shown in FIG. 7 and Table 2, nickel, fluorine and phosphorous were present in an outermost layer 508 of the outer wall of the nozzle. The outermost layer was 2 µm in thickness. Nickel, fluorine and phosphorous were also present in a foundation layer 507 underneath the outermost layer 508. The foundation layer was 3 µm in thickness. Nickel derived from SUS constituents was present in a treated SUS layer, though fluorine and phosphorous were not present therein. Also from the viewpoint of the contact angles shown in Table 1 and the elemental analysis results shown in Table 2, it is understood that the nozzle's outer wall surface is highly water-repellent. It has been confirmed that the lot-to-lot uniformity of treated cells is also high.

Water-repellency finishing may be performed on outer wall surfaces of the pipetting nozzle by silane coupling treatment, by vapor deposition of water-repellent molecules, by superhydrophobic electroplating, or by diamond-like carbon treatment. The sample pipetting nozzle may be water-repellency treated, so that at least an outer wall area and an edge face of the nozzle's tip to be immersed in a sample is water-repellency treated.

(2) Hydrophilization of Cell's Pipetting Area

A reaction cell (hereinafter referred to as the "cell") for an autoanalyzer was fabricated by injection molding using poly cyclo olefin as the material of the cell. As the cell material, it is possible to use one type of material selected from the group consisting of poly cyclo olefin resin, polycarbonate resin, acrylic resin, and polystyrene resin. From the viewpoint of a low water absorption coefficient, low moisture vapor permeability, high total light transmittance, a low refractive index, and a low mold shrinkage factor, it is desirable to select poly cyclo olefin resin. Poly cyclo olefin is a high polymer and the main and side chains thereof are respectively composed of carbon-carbon bonds and carbon-hydrogen bonds. A cyclic saturated hydrocarbon exists in some main chains. In an autoanalyzer, a sample and a reagent are reacted with each other in individual unit cells to measure the color development of pigments and a latex agglutination phenomenon by a change in the optical transmittance of a plurality of specific wavelengths.

Each unit cell is typically a vertically long container having an opening at an upper end thereof and provided with a resin bottom wall and a side wall erected upward from a rim of the bottom wall. The bottom wall can be formed into a rectangular or a square shape. In this case, an opposing pair of (two) portions, among four portions composing the side wall, forms photometrical faces through which light for measurement transmits. The other opposing pair of (two) portions forms non-photometrical faces through which light for measurement does not transmits.

Figure 9:
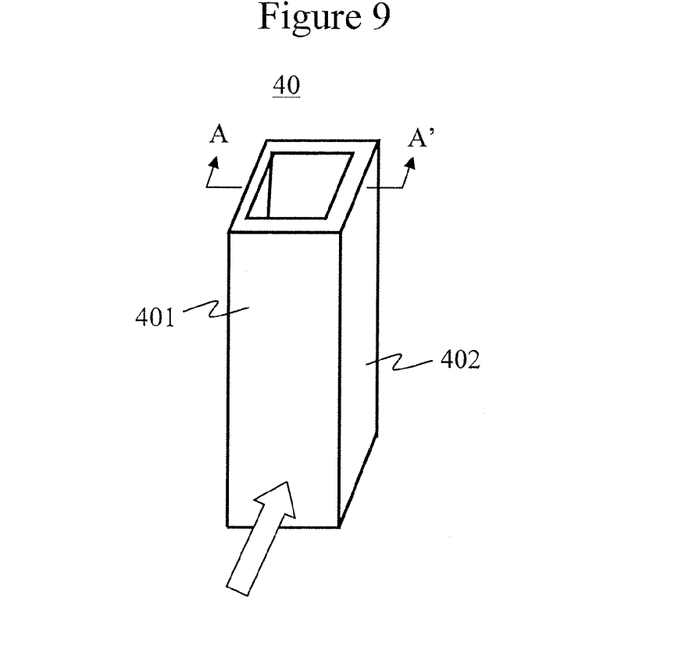
FIG. 9 is a perspective external view of a reaction cell.
Figure 10:
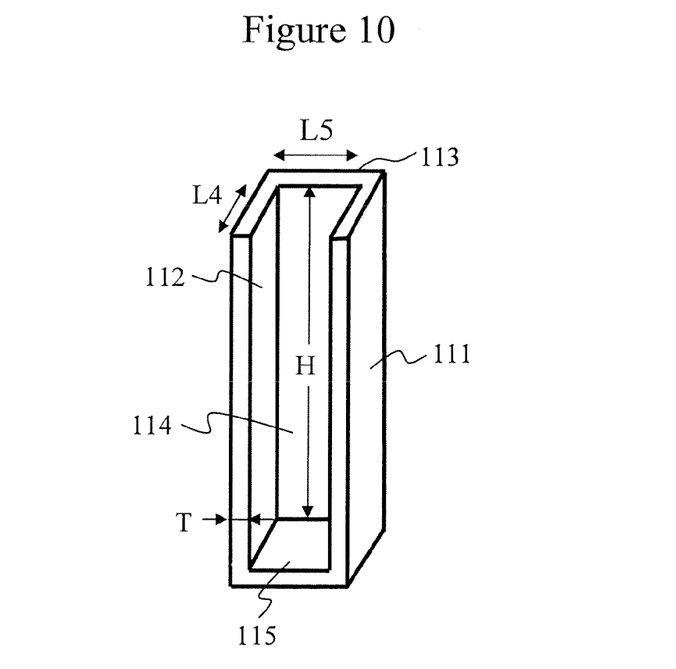
FIG. 10 is a cross-sectional view of the reaction cell.

FIG. 9 illustrates a perspective external view of a cell. A cell 40 includes a photometrical face 401 and a non-photometrical face 402. Photometrical light enters the photometrical face 401 from a direction denoted by an arrow. FIG. 10 illustrates a cross-sectional view taken by cutting the cell 40 along a line A-A'.

Figure 11:
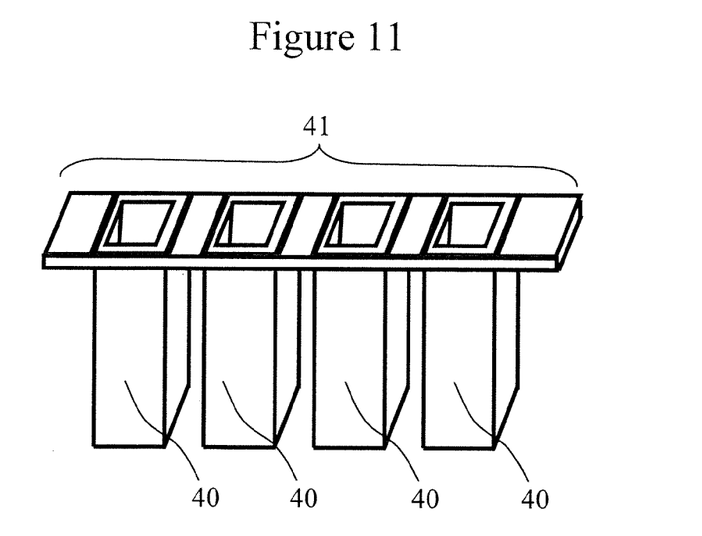
FIG. 11 is a perspective external view of a cell block formed by integrally molding a plurality of reaction cells.

The cell 40 includes an outer non-photometrical surface 111, an inner non-photometrical surface 112, an outer photometrical surface 113, an inner photometrical surface 114, and an inner bottom wall surface (bottom face) 115. Dimensions of inner walls of the cell are set so that a length L4 half the length of the non-photometrical face is 3 mm, a length L5 of the photometrical face is 4 mm, a height H is 30 mm, and a cell wall thickness T is 1 mm. The cell includes a closed portion formed by the bottom wall 115 and an open portion 140 above the bottom wall. Note that a cell block 41 integrally molded by laying out a plurality of cells 40 in a line so that openings of respective cells face in the same direction as illustrated in FIG. 11 may be used, and surfaces of the respective cells may be hydrophilized.

Approximately 0.5 mL of ethanol was injected into a cell 40 and allowed to stand for 24 hours, thereby removing ethanol. Thereafter, the cell was put in a vacuum desiccator and dried, thereby cleaning the cell's inner surfaces. Note that no practical problems are caused even if corona discharge treatment described below is carried out without performing this cleaning by ethanol.

Figure 12:
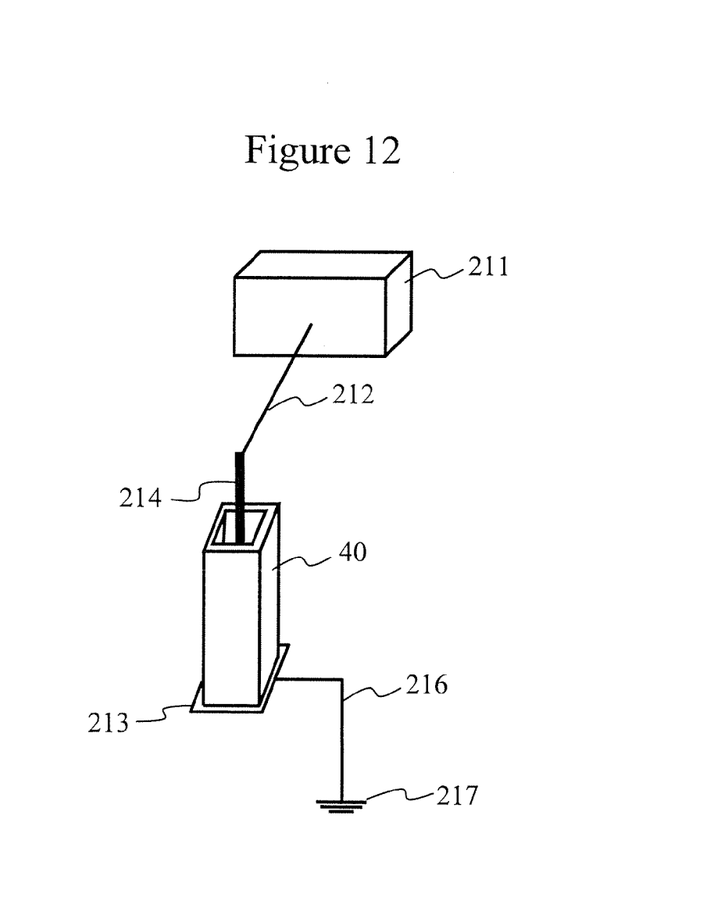
FIG. 12 is a schematic view of corona-discharge treatment.

FIG. 12 illustrates a schematic view of partial corona discharge treatment. A cathode plate 213 was placed on the outside of the bottom face of the cell 40 cleaned and dried after being molded using resin. The cathode plate was connected to a ground 217 through a wire 216. A bar electrode 214 which was an anode of corona discharge was placed inside the cell 40 toward the center of the cell's bottom face to a height of 1 mm from the bottom face. The lower end of the bar electrode 214 was 2 mm in diameter and 50 mm in length, and was connected to a corona discharge power supply 211 through the wire 212. As the corona discharge power supply, a pulsed discharge source capable of counting the number of discharge pulses is desired. Alternatively, a high-frequency discharge source may be used. In the present embodiment, a pulsed corona discharge source was used. By applying a voltage of 25 kV, the cell's bottom face was corona discharge-treated. A pulse interval was set to 300 pulses per second, and the bottom face was treated for one second, i.e., with 300 pulses. From generated voltage and current values, it was confirmed on an oscilloscope that an energy of approximately 5 joule was produced if corona discharge treatment was performed under this condition. As an ambient gas, air was used in the present embodiment to perform corona discharge treatment. Alternatively, corona discharge treatment may be performed under a nitrogen atmosphere. In the present embodiment, cells were corona discharge-treated one at a time. If a plurality of cells is integrally molded as a multiple cell block, however, the plurality of cells may be corona discharge-treated at the same time.

Figure 13:
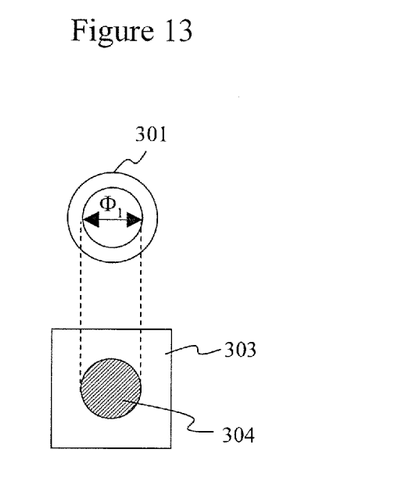
FIG. 13 is a schematic view of a hydrophilized bottom of a reaction cell.

FIG. 13 illustrates a condition in which the pipetting mechanism is viewed from above. Assume that an inner diameter of a pipetting nozzle tip 301 is $\phi_1$ and the size of a hydrophilized area 304 in a cell bottom 303 is S. If the size S is equal to the inner area of the nozzle, i.e., if $S=\pi(\phi_1)^2$, then a sample can be sufficiently transferred. Even if $S>\pi(\phi_1)^2$, the sample can be sufficiently transferred to a hydrophilized area of the cell bottom. A further advantageous effect is produced by correctly varying S according to the amount of pipetting. Changes can be made to the size and shape of the hydrophilized area S by masking portions of each cell not desired to be discharge-treated, by using a material the same as the material of the cells when corona discharge treatment is performed.

In the present embodiment, the hydrophilized area of the bottom face was set as $S=\pi(\phi_1)^2$ and $\phi_1=0.3$ mm. For contact angle measurement, Drop Master 500 made by Kyowa Interface Science was used. 1 μL of pure water was dropped on a modified surface by using a syringe to measure static contact angles one second after droplet deposition by a three-point method. For the measurement, three treated samples were prepared and an average value of the samples was determined. As a result, while contact angles of cell surfaces before surface modification and of non-modified portions were approximately 90 degrees, the contact angles decreased to 75 degrees when surface modification was made. The maximum variation of measured values (maximum value–minimum value) was approximately 3 degrees or less.

(3) Study on the Possibility of Pipetting by Combination of Water-Repellent Nozzle and Hydrophilized Cell In a pipetting mechanism in which a sample was discharged into a cell by using a pipetting nozzle, an evaluation was made of pipetting performance based on the combination of a water-repellent nozzle discussed in item (1) and a cell with a hydrophilized bottom face discussed in item (2). The pipetting nozzle used was made of SUS 304, and 0.3 mm in inner diameter and 0.5 mm in outer diameter. In order to determine a contact angle of the nozzle's surface, a contact angle when 0.2 μL, of pure water was dropped onto a nozzle tip was measured by the above-described method. The contact angle of a new pipetting nozzle was 90°, and then decreased to 10° after cleaning with a cleaning liquid. Accordingly, the contact angle of an SUS 304 nozzle for mounting on actual equipment is 10°. In addition, an evaluation was made of a water-repellency treated pipetting nozzle having a contact angle of 120°.

On the other hand, the contact angle of a cell surface which is a destination of sample discharge (transfer) was 90° in the past, and the contact angle of a cell hydrophilized by corona discharge is 75°. A determination was made visually on the possibility of pipetting by using three types of pipetting nozzles ((A) SUS nozzle after cleaning, (B) new SUS nozzle, and (C) water-repellent nozzle) and two types of cells (conventional cell and hydrophilized cell) as destinations of pipetting and by combining respective nozzles and cells. A study was made by setting the amounts of pipetting to 0.2 μL, 0.4 μL and 0.5 μL. With the respective amounts of water being discharged from each pipetting nozzle, the nozzle was lowered at a rate of 1 cm/min. Then, the nozzle was lifted also at a rate of 1 cm/min when the water came into contact with a surface of the cell bottom. If water attaches to an outer wall of the lifted nozzle and is thus carried over, the amount of pipetting (transfer) decreases. Predetermined amounts of water were ejected respectively from the above-described three types of nozzles, transferred onto surfaces of cycloolefin polymer, and the amounts of water transferred onto the cycloolefin polymer surfaces were read from images of a contact angle meter. For the contact angle meter, Drop Master 500 made by Kyowa Interface Science was used. A droplet of a predetermined amount of pure water was formed at a syringe tip, and transferred onto a surface of a cell made of cycloolefin polymer. Evaluations were made 10 times, and a case in which transfer resulted in failure even once was rated as "untransferable." In addition, an estimate was made of the amount of transfer onto the cell surface from images of the contact angle meter when transfer resulted in failure.

(A) In the Case of 0.2 μL Pipetting

Table 3 summarizes the results of quantifying pipetting when 0.2 μL of water was pipetted. A predetermined amount of water was ejected from an SUS syringe needle, transferred onto a surface of each cycloolefin polymer cell, and the amount of water transferred onto the cell surface was read from an image of a contact angle meter. For the contact angle meter, Drop Master 500 made by Kyowa Interface Science was used. A droplet of a predetermined amount of pure water was formed at a syringe tip, and transferred onto a surface of cycloolefin polymer. The results of evaluation are shown below.

(a) When an SUS pipetting nozzle after cleaning (10° contact angle) was used, pipetting (transfer) was not possible if a surface of a destination of sample transfer was of either a hydrophilized cell (75° contact angle) or of a conventional cell (90° contact angle). For a pipetted amount of 0.2 μL, the amount of transfer onto the cell surface was 0.1 μL.

(b) When a new SUS pipetting nozzle (90° contact angle) was used, pipetting (transfer) was not possible if a surface of a destination of sample transfer was of either a hydrophilized cell (75° contact angle) or of a conventional cell (90° contact angle). Although 0.2 μL of water was desired to be pipetted, the amount of transfer onto the cell surface was 0.1 μL.

(c) When a water-repellent pipetting nozzle (120° contact angle) was used, pipetting (transfer) to a hydrophilized cell (75° contact angle) was perfectly possible. For an intended pipetting of 0.2 μL, it was possible to completely transfer 0.2 μL of water onto the cell surface. When a water-repellent pipetting nozzle (120° contact angle) was used, the amount of transfer to the conventional cell (90° contact angle) was 0.1 μL, and therefore, transfer resulted in failure.

From these results, it proved that for a microscale pipetting of 0.2 μL, transfer was possible only when a water-repellency treated nozzle and a hydrophilized cell were combined.

TABLE 3

Amounts of Droplet Deposition on Cells in 0.2 μL Pipetting

| | | Pipetting nozzle (contact angle) | | |
|---|---|---|---|---|
| | | (A) Nozzle after cleaning (10°) | (B) New nozzle (90°) | (C) Water-repellent nozzle (120°) |
| Cell | Hydrophilized cell (75° contact angle) | 0.1 μL (Untransferable) | 0.1 μL (Untransferable) | 0.2 μL (Transferable) |
| | Conventional cell (90° contact angle) | 0.1 μL (Untransferable) | 0.1 μL (Untransferable) | 0.1 μL (Untransferable) |

(B) In the Case of 0.4 μL Pipetting

Table 4 summarizes the results of quantifying pipetting when 0.4 μL of water was pipetted.

(a) When an SUS pipetting nozzle after cleaning (10° contact angle) was used, pipetting (transfer) was not possible if a surface of a destination of sample transfer was of either a hydrophilized cell (75° contact angle) or of a conventional cell (90° contact angle). Although 0.4 μL of water was desired to be pipetted, the amount of transfer onto the cell surface was 0.3 μL.

(b) When a new SUS pipetting nozzle (90° contact angle) was used, pipetting (transfer) was not possible if a surface of a destination of sample transfer was of either a hydrophilized cell (75° contact angle) or of a conventional cell (90° contact angle). Although 0.4 μL of water was desired to be pipetted, the amount of transfer onto the cell surface was 0.3 μL.

(c) When a water-repellent pipetting nozzle (120° contact angle) was used, pipetting (transfer) to a hydrophilized cell (75° contact angle) was perfectly possible. For an intended pipetting of 0.4 μL, it was possible to completely transfer 0.4 μL of water onto the cell surface. When a water-repellent pipetting nozzle (120° contact angle) was used, the amount of transfer to the conventional cell (90° contact angle) was 0.3 μL, and therefore, transfer resulted in failure.

From these results, it proved that for a microscale pipetting of 0.4 μL, transfer was possible only when a water-repellency treated nozzle and a hydrophilized cell were combined.

Here, the following shows an example of a 0.5 μL pipetting test as a comparative example of experiments.

(C) In the Case of 0.5 μL Pipetting

Table 5 summarizes the results of quantifying pipetting when 0.5 μL of water was pipetted.

(a) When an SUS pipetting nozzle after cleaning (10° contact angle) was used, pipetting (transfer) was possible if a surface of a destination of sample transfer was of a hydrophilized cell (75° contact angle). For an intended pipetting (transfer) of 0.5 μL, it was possible to completely transfer 0.5 μL of water. On the other hand, pipetting (transfer) was not possible if the transfer destination was a conventional cell (90° contact angle). Although 0.5 μL of water was desired to be pipetted, the amount of transfer onto the cell surface was 0.4 μL.

(b) When a new SUS pipetting nozzle (90° contact angle) was used, pipetting (transfer) was possible whether a surface of a destination of sample transfer was of a hydrophilized cell (75° contact angle) or of a conventional cell (90° contact angle). For an intended pipetting (transfer) of 0.5 μL it was possible to completely transfer 0.5 μL of water. However, if an SUS 304 nozzle was used without performing surface water-repellency treatment thereon, the nozzle, in practice, went into the same condition (10° contact angle) as that of the nozzle after cleaning after several times of use. Accordingly, transfer onto the conventional cell was not possible for practical purposes.

(c) When a water-repellent pipetting nozzle (120° contact angle) was used, pipetting (transfer) to a hydrophilized cell (75° contact angle) was perfectly possible. For an intended pipetting of 0.5 μL, it was possible to completely transfer 0.5 μL of water onto the cell surface. When a water-repellent pipetting nozzle (120° contact angle) was used, the amount of transfer to the conventional cell (90° contact angle) was 0.5 μL, and therefore, transfer resulted in success.

TABLE 4

Amounts of Droplet Deposition on Cells in 0.4 μL Pipetting

| | | Pipetting nozzle (contact angle) | | |
|---|---|---|---|---|
| | | (A) Nozzle after cleaning (10°) | (B) New nozzle (90°) | (C) Water-repellent nozzle (120°) |
| Cell | Hydrophilized cell (75° contact angle) | 0.3 μL (Untransferable) | 0.3 μL (Untransferable) | 0.4 μL (Transferable) |
| | Conventional cell (90° contact angle) | 0.3 μL (Untransferable) | 0.3 μL (Untransferable) | 0.3 μL (Untransferable) |

TABLE 5

Amounts of Droplet Deposition on Cells in 0.5 μL Pipetting

| | | Pipetting nozzle (contact angle) | | |
|---|---|---|---|---|
| | | (A) Nozzle after cleaning (10°) | (B) New nozzle (90°) | (C) Water-repellent nozzle (120°) |
| Cell | Hydrophilized cell (75° contact angle) | 0.5 μL (Transferable) | 0.5 μL (Transferable) | 0.5 μL (Transferable) |
| | Conventional cell (90° contact angle) | 0.4 μL (Untransferable) | 0.4 μL (Untransferable) | 0.5 μL (Transferable) |

From the results of Experiments (A) to (C), it proved that transfer was possible for 0.4 μL or less microscale pipetting by combining a water-repellency treated nozzle and a hydrophilized cell. Note that for pipetting nozzles used in this experiment, it was possible to make a transfer onto the cell's bottom face with less difficulty as a nozzle's diameter was decreased. It was possible to achieve pipetting of 0.4 μL or less droplets, in particular, by setting the inner diameter of the nozzle to 0.5 mm or smaller and the outer diameter thereof to 1.0 mm or smaller.

Figure 14:
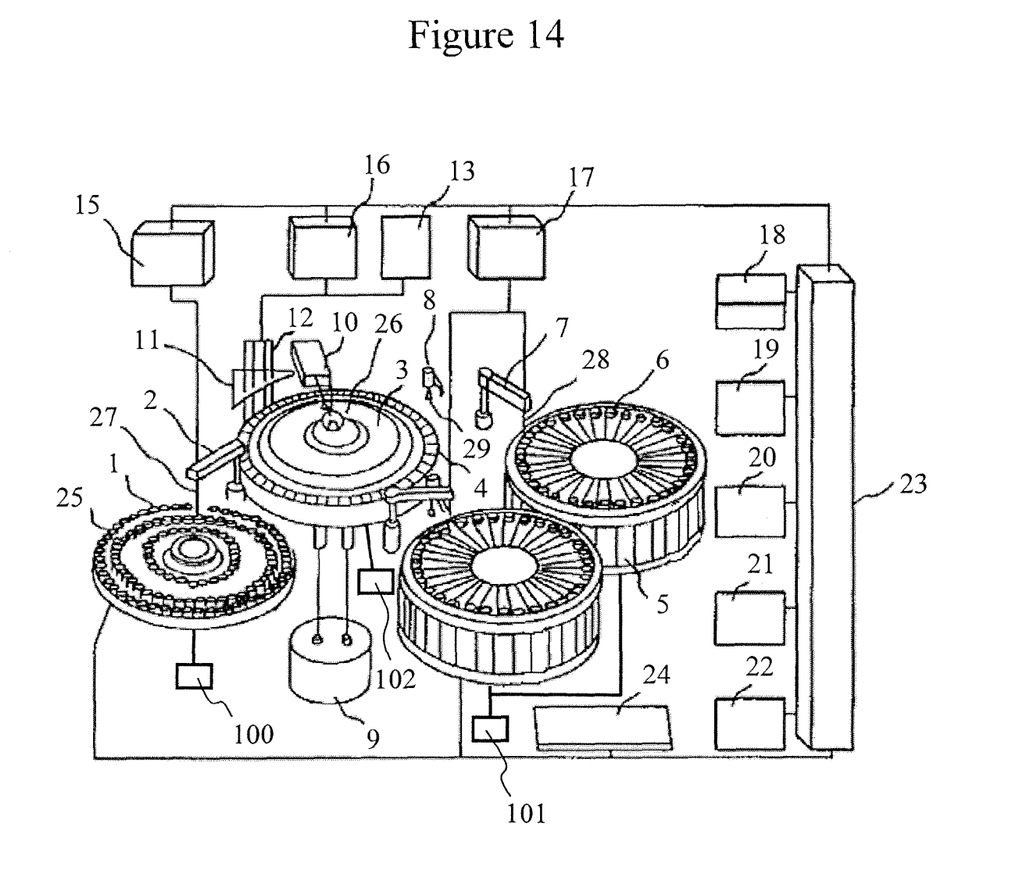
FIG. 14 is a drawing illustrating a configuration example of an autoanalyzer.

(4) Autoanalyzer Using both Sample Pipetting Nozzle with Water-Repellent Outer Wall Surfaces and Cell with Hydrophilized Bottom Face A description will be given of an embodiment of automatic analysis using both the "sample pipetting nozzle with water-repellent outer wall surfaces and hydrophilic inner wall surfaces" fabricated in item (1) discussed above and the "cell with a hydrophilized bottom face" fabricated in item (2) discussed above. FIG. 14 is a drawing illustrating a configuration example of an autoanalyzer according to the present invention.

One or more sample cells 25 are disposed in a sample storage mechanism 1. Although a sample disk mechanism which is a disk-like sample storage mechanism is shown here, the mechanism may have a shape of a sample rack or a sample holder. In addition, the term "sample" as referred to herein refers to a solution under test to be used for reaction in a reaction cell. The sample may be a concentrate solution of a collected sample, or a solution prepared by applying processing treatment, such as dilution or pretreatment, to the concentrate solution. A sample in a sample cell 25 is taken up by a water-repellent sample pipetting nozzle 27 of a pipetting mechanism for sample supply 2 and injected into a predetermined reaction cell. The outer wall surfaces of this water-repellent sample pipetting nozzle 27 are water-repellent plating treated as described in item (1) discussed above, and therefore, are water-repellent. The inner wall surfaces of the nozzle are made of metal and are hydrophilic. A reagent disk mechanism 5 is provided with a multitude of reagent containers 6. In addition, a pipetting mechanism for reagent supply 7 is arranged in a mechanism 5. A reagent is suctioned by a reagent pipetting nozzle 28 of this mechanism 7, and injected into a predetermined reaction cell. For the reagent pipetting nozzle, a nozzle the tip of which is also water-repellent plating treated may be used. In the present embodiment, a reagent pipetting nozzle the outer wall surfaces of which were water-repellent plating treated in the same way as the nozzle 27 was used. Reference numeral 10 denotes a spectral photometer and reference numeral 26 denotes a light source with a condensing filter. A reaction disk 3 for housing measuring objects is located between the spectral photometer 10 and the light source with a condensing filter 26. 120 reaction cells 4 with hydrophilized bottom faces are disposed on an outer circumference of this reaction disk 3. In addition, the whole of the reaction disk 3 is maintained at a predetermined temperature by a thermostatic chamber 9. Reference numeral 11 denotes a reaction cell cleaning mechanism, and a cleaning agent is supplied from a cleaning agent container 13.

Reference numeral 19 denotes a computer, reference numeral 23 denotes an interface, reference numeral 18 denotes a logarithmic converter and an A/D converter, reference numeral 17 denotes a pipetter for reagents, reference numeral 16 denotes a rinse water pump, and reference numeral 15 denotes a pipetter for samples. In addition, reference numeral 20 denotes a printer, reference numeral 21 denotes a CRT, reference numeral 22 denotes a floppy disk or a hard disk as a storage device, and reference numeral 24 denotes an operating panel. The sample disk mechanism, the reagent disk mechanism, and the reaction disk are controlled and driven through the interface by a driving unit 100, a driving unit 101, and a driving unit 102, respectively. In addition, respective units of the autoanalyzer are controlled by the computer through the interface.

In the above-described configuration, an operator inputs analysis request information by using the operating panel 24. The analysis request information input by the operator is stored in a memory within a microcomputer 19. A sample to be measured put in a sample cell 25 and set in a predetermined position of the sample disk housing mechanism 1 is pipetted into a reaction cell in predetermined amounts, according to the analysis request information stored in the memory of the microcomputer 19, by the sample pipetter 15 and the nozzle 27 of the pipetting mechanism for sample supply 2. The sample pipetting nozzle 27 is rinsed with water. A predetermined amount of reagent is pipetted into the abovementioned reaction cell by the reagent nozzle 28 of the pipetting mechanism for reagent supply 7. The reagent nozzle 28, after being rinsed with water, pipettes a reagent for the next reaction cell. A mixed solution of a sample and a reagent is agitated by an agitating rod 29 or an ultrasonic device of an agitation mechanism 8. The agitation mechanism 8 sequentially agitates mixed solutions of the next and subsequent reaction cells.

Each reaction cell 4 is maintained at a constant temperature by the thermostatic chamber 9 and serves as both reaction and photometrical containers. Light is supplied from the light source with a condensing filter 26 in the course of reaction, and a reaction solution is photometrically measured by the spectral photometer 10 at regular time intervals. The absorbance of the mixed solution is measured using one or more than one preset wavelength. By using the light source with a condensing filter at the time of measurement, it is possible to let light selectively pass through only the hydrophilic portion of the reaction cell.

As described above, use of both a water-repellent sample pipetting nozzle and a cell with a hydrophilized bottom face enables 0.4 μL or less sample pipetting. This allows for precise pipetting (transfer) and, thereby, enables the accuracy of subsequent analyses to be maintained high. Consequently, it is possible to greatly reduce the amounts of sample and reagent to be put in a reaction cell. This is useful from the viewpoint of reduction in running costs. By using a water-repellency treated pipetting nozzle and a hydrophilization-treated reaction cell of the present invention, it was possible to conduct automatic analysis with the amount of reaction solution prepared by mixing a reagent and a sample solution reduced to a half or less, compared with a case in which a conventional stainless steel pipetting nozzle and a conventional reaction cell were used.

The measured absorbance is loaded into the computer 19 though the logarithmic converter, and the A/D converter 18, and the interface 23. The loaded absorbance is converted into a concentration value, and the concentration value is stored in a floppy or hard disk 22 and/or output to the printer 20. In addition, inspection data can be displayed on the CRT 21. A reaction cell 4 in which measurement is completed is rinsed with water by the reaction cell cleaning mechanism (nozzle arm) 11. Water in reaction cells in which cleaning is completed is suctioned by a suction nozzle 12, and the reaction cells are sequentially used for the next and subsequent analyses.

Automatic analysis was conducted by equipping an autoanalyzer with pipetting nozzles having water-repellency treated portions and cells with hydrophilized bottom faces, as described above. As a result, it has proved that it is possible to sufficiently reduce sample attachments and rinse water attachments. It is also possible to conduct consistent automatic analysis without causing any mutual contamination and carry-over. In addition, a sample can be reliably transferred onto a surface of a cell's bottom face and maintain high pipetting accuracy. At the same time, this nozzle has electrical conductivity and the function of detecting the fluid levels of a reaction solution and a sample.

| Reference Signs List | |
| --- | --- |
| 1 | Sample storage mechanism |
| 2 | Pipetting mechanism for sample supply |
| 3 | Reaction disk |
| 4 | Reaction cell |
| 5 | Reagent disk mechanism |
| 6 | Reagent container |
| 7 | Pipetting mechanism for reagent supply |
| 25 | Sample cell |
| 27 | Sample pipetting nozzle |
| 28 | Reagent nozzle |
| 40 | Cell |
| 41 | Cell block |
| 51 | Reaction cell |
| 53 | Sample cell |
| 56 | Sample pipetting mechanism |
| 59 | Cleaning mechanism |
| 70 | Sample pipetting nozzle |
| 100 | Driving unit |
| 101 | Driving unit |
| 102 | Driving unit |
| 211 | Corona discharge source |

| Reference Signs List | |
| --- | --- |
| 213 | Bottom electrode |
| 214 | Bar electrode |
| 303 | Cell bottom |
| 304 | Hydrophilized area |
| 506 | SUS |
| 507 | Foundation layer |
| 508 | Water-repellent layer |
| 509 | Plated layer |
| 560 | Arm |
| 561 | Sample pipetting nozzle |
| 562 | Pillar |
| 563 | Sample |
| 564 | Adhering sample |
| 53 | Sample cell |
| 565 | Adhering sample |
| 566 | Adhering rinse water |

The invention claimed is:

1. An autoanalyzer comprising:
a sample cell to put a sample in;
a reagent container to put a reagent in;
a reaction cell for the sample and the reagent to be injected into;
a sample pipetting mechanism for pipetting the sample in the sample cell into the reaction cell;
a reagent pipetting mechanism for pipetting the reagent in the reagent container into the reaction cell;
wherein:
the sample pipetting mechanism includes a sample pipetting nozzle,
the sample pipetting nozzle is made of a base material having an outer wall surface, a first layer formed on the outer surface of the nozzle, and a second layer is formed on the first layer,
the base material is stainless steel,
the first layer includes nickel,
the second layer includes nickel, fluorine and phosphorus,
thickness of the second layer is thinner than thickness of the first layer,
the outer wall surface of the nozzle is water-repellent,
an inner wall surface of the nozzle is more hydrophilic than the outer wall surface of the nozzle,
the bottom face of the reaction cell is more hydrophilic than the inner wall surface of the nozzle, and
the nozzle has electrical conductivity.

2. The autoanalyzer according to claim 1,
wherein the reaction cell has a hydrophilization-treated bottom face.

3. The autoanalyzer according to claim 1,
wherein the tip of the sample pipetting nozzle is 0.5 mm or less in inner diameter and 1.0 mm or less in outer diameter.

4. The autoanalyzer according to claim 1,
wherein the first layer and the second layer are separately formed in different steps.

* * * * *